United States Patent [19]
Ripart

[11] Patent Number: 5,776,165
[45] Date of Patent: Jul. 7, 1998

[54] ACTIVE IMPLANTABLE CARDIAC DEFIBRILLATOR CARDIOVERTER AND METHOD OF OPERATION

[75] Inventor: Alain Ripart, Gif sur Yvette, France

[73] Assignee: Ela Medical S.A., Montrouge, France

[21] Appl. No.: 745,808

[22] Filed: Nov. 8, 1996

[30] Foreign Application Priority Data

Oct. 11, 1995 [FR] France .................... 95 13362

[51] Int. Cl.[6] .......................... A61N 1/39
[52] U.S. Cl. .......................... 607/5
[58] Field of Search .......................... 607/5

[56] References Cited

U.S. PATENT DOCUMENTS

| | | | |
|---|---|---|---|
| 5,224,476 | 7/1993 | Ideker et al. | |
| 5,306,241 | 4/1994 | Kroll et al. | 607/5 |
| 5,360,435 | 11/1994 | DeGroot | 128/419 PG |
| 5,376,103 | 12/1994 | Anderson et al. | 128/419 PG |
| 5,411,528 | 5/1995 | Miller et al. | 607/5 |
| 5,470,341 | 11/1995 | Kuehn et al. | 607/5 |
| 5,545,181 | 8/1996 | Jacobson et al. | 607/4 |
| 5,545,783 | 8/1996 | Altman | 607/5 |

FOREIGN PATENT DOCUMENTS

| | | | |
|---|---|---|---|
| 0253505A2 | 6/1987 | European Pat. Off. | A61N 1/365 |
| 0522693A1 | 5/1992 | European Pat. Off. | A61N 1/39 |
| WO95/16494 | 6/1995 | WIPO | A61N 1/39 |

OTHER PUBLICATIONS

Florin et al., "The Induction of Atrial Fibrillation with Low energy Defibrillator Shocks is Related to Lead and Pulse Width," *Supplement To Circulation* vol. 92 No. 8, Oct. 15,1995, Abstracts from the 68th Scientific Sessions Anaheim Convention Center, Arahein CA Nov. 13–16, 1995 p. 143, Abstract No. 667.

*Primary Examiner*—William E. Kamm
*Attorney, Agent, or Firm*—Orrick Herrington & Sutcliffe LLP

[57] ABSTRACT

An active implanted medical device of the implantable defibrillatory cardioverter type. This device comprises an atrial electrode (40), a ventricular electrode (50), at least one electrode external to the heart (70, 80) and a pulse generator (60). The pulse generator comprises a means for delivering a shock energy pulse for defibrillation or cardioversion, and means for switching the electrode configuration, that determines between which electrodes the defibrillation or cardioversion shock energy pulse is to be applied. The switching means operates in response to the determined delivery of a cardioversion shock pulse energy, by disconnecting the atrial electrode from the means for delivering the shock energy pulse for defibrillation or cardioversion, and, if the configuration of electrodes determined by the switching means foresees the commutation of the atrial electrodes a return electrode, then to substitute for the atrial electrode at least one of electrodes external to the heart.

8 Claims, 3 Drawing Sheets

|                  | H1 | L1 | H2 | L2 | H3 | L3 |
|------------------|----|----|----|----|----|----|
| V/A              | 0  | 0  | 1  | 0  | 0  | 1  |
|                  | 0  | 0  | 0  | 1  | 1  | 0  |
| V/EXTERNAL       | 0  | 1  | 1  | 0  | 0  | 0  |
|                  | 1  | 0  | 0  | 1  | 0  | 0  |
| V/EXTERNAL + A   | 0  | 1  | 1  | 0  | 0  | 1  |
|                  | 1  | 0  | 0  | 1  | 1  | 0  |
| A+V/EXTERNAL     | 0  | 1  | 1  | 0  | 1  |    |
|                  | 1  | 0  | 0  | 1  | 0  | 1  |

CARDIOVERSION

| | | |
|---|---|---|
| V/A | → | V/EXT |
| V/EXT + A | → | V/EXT |
| A+V/EXT | → | V/EXT |

FIG. 3

ACTIVE IMPLANTABLE CARDIAC DEFIBRILLATOR CARDIOVERTER AND METHOD OF OPERATION

FIELD OF THE INVENTION

The present invention concerns an active implantable medical device such as those defined in the Jun. 20, 1990 directive 90/385/EEC of the European Community Council, and more particularly to the family of devices that delivers to the heart electrical shock impulses of high energy, that is to say shock pulses having an energy level exceeding the energy level normally provided to achieve simple cardiac stimulation (pacing), with a view to terminate a tachyarrhythmia. These devices are commonly called "implantable defibrillators" or "cardioverters." It should be understood, however, that the present invention also concerns implantable defibrillators/cardioverters/pacemakers, as well as implantable defibrillators/pacemakers.

BACKGROUND OF THE INVENTION

Active implantable medical devices that deliver a shock energy pulse typically have two components, namely a pulse generator and a lead system. The pulse generator functions to supervise the cardiac activity and to generate a high energy pulse when the heart presents a ventricular arrhythmia that is susceptible to be treated, that is, reverted by a shock energy pulse. When this shock energy pulse is approximately between 0.1 and 10 J, one designates this therapy by the name of "cardioversion," and the electrical shock is called a "cardioversion shock". When the shock energy level is greater than approximately 10 J, the therapy is known by the name defibrillation, and the electrical shock is called a "defibrillation shock". The pulse generator typically includes the logic to identify from the supervised cardiac activity when the heart has a ventricular arrhythmia, and to classify the type of arrhythmia to select the appropriate therapy. This aspect of the pulse generator does not form a part of the present invention.

The lead system is connected to the pulse generator and comprises one or several leads (also known as probes) which have electrodes that operate to distribute to the heart the shock pulse energy in an appropriate manner. Several different lead system electrode configurations are known, such as are described, for example, in U.S. Pat. No. 5,376,103. One configuration that is often employed uses two electrodes, one of which is placed at the apex of the right ventricle, and the other of which is placed in the vicinity of the atrium, for example, in the coronary sinus or inside the atrium. In the following discussion, this last electrode is designated by the general term "atrial electrode", which means that it is situated in the atrium or in the vicinity of the atrium, as the case may be.

In addition, it is foreseen that there is at least one electrode external to the heart in the lead system. This external electrode can be the case of the pulse generator and/or a subcutaneous electrode, called a "patch electrode". The external electrode has a greater surface than the atrial electrode, and serves as an electrode(s) for the collection of the current injected from the interior of the heart, and also is referred to as a return electrode.

In summary, the lead system comprises, on the one hand, an atrial electrode and a ventricular electrode and, on the other hand, one or more electrodes external to the heart.

The cardioversion or defibrillation shock can be delivered according to several known electrode configurations. These various electrode configurations, which are generally known and some of which are described hereafter, are chosen by internal commutation circuits situated in the pulse generator. One thus optimizes the efficiency of the shock by choosing the electrode configuration that is appropriate to the state of the patient. The various possible electrode configurations include the following:

a) the shock pulse is delivered between the ventricular electrode and the atrial electrode;

b) the shock pulse is delivered between the ventricular electrode and one of the external electrodes to the heart (wherein the external electrode is the case or the patch electrode);

c) the shock pulse is delivered between, on the one hand, the ventricular electrode and, on the other hand, the lead subsystem formed by the atrial electrode and the case and/or the patch electrode connected together, with the electrical connections between these two or three electrodes being realized at the moment of the deliverance of the shock;

d) the shock is delivered between, on the one hand, the lead subsystem formed by the atrial electrode and the ventricular electrode connected together at the moment of the deliverance of the shock, and, on the other hand, the case and/or the patch electrode. In one variation of the electrode configuration b), the two external electrodes are in addition electrically connected together at the moment of the deliverance of shock in a manner to increase the volume of the cardiac muscle through which the electrical current passes. These various configurations are described in detail in international application publication WO-A-95/16494.

The manner in which one can operate the different commutations inside the case in order to attain one of these various electrode configurations is, for example, described in the aforementioned U.S. Pat. No. 5,376,103. By an appropriate choice of the electrode configuration, one can thus optimize the cardioversion or defibrillation shock delivery according to the situation of the patient, as identified by the pulse generator (or some other device).

It has nevertheless been observed (Florin et al., "The Induction of Atrial Fibrillation with Low Energy Defibrillator Shock is related to Lead and Pulse Width", *Supplement to Circulation*, Vol. 92, No. 8, 15 Oct. 1995, Abstracts from the 68th Scientific Sessions, Anaheim Convention Center, Anaheim, Calif., Nov. 13–16, 1995, p. 143, abstract No. 0667) that, in the case of the electrode configurations a), c) and d) described above, after the deliverance of a cardioversion pulse, a significant proportion of patients develop an atrial fibrillation. In others words, although the cardioversion shock reduces efficiently the disturbance of the ventricular rhythm, in doing so it creates a risk of occurrence of an atrial arrhythmia. Indeed, in the known configurations a), c) and d) above, the atrial electrode is used for the deliverance of the cardioversion shock, and it circulates, therefore, a current whose intensity operates to terminate (stop) the ventricular tachyarrhythmia including defibrillation, but that is sufficiently large that there is a risk of inducing an atrial fibrillation.

OBJECTS AND SUMMARY OF THE INVENTION

It is, therefore, an object of the present invention to minimize, or to suppress, the aforementioned disadvantage of inducing atrial arrhythmia during a ventricular cardioversion.

Broadly, the present invention is directed to an apparatus and method for terminating a ventricular tachyarrhythmia,

3

The device of the invention is of the general type comprising an atrial electrode placed in the vicinity of or inside the atrium, a ventricular electrode placed inside the ventricle, at least one electrode external to the heart, and a pulse generator The pulse generator includes circuits for delivering a defibrillation or cardioversion shock energy pulse and a switch network for selectively commuting the electrode configuration, which operates to determine between which electrodes the defibrillation or cardioversion shock energy is to be applied.

In accordance with the present invention, the pulse generator comprises, in addition a means, responsive to a determination that a cardioversion shock energy has to be delivered, for operating the switch network to disconnect the atrial electrode from the circuit that will deliver the cardioversion shock energy pulse, and, if the determined electrode configuration anticipates the commutation of the atrial electrode to the shock pulse delivery circuit, to substitute for the atrial electrode at least one of the electrodes external to the heart.

Preferably, the pulse generator includes logic control circuits for identifying the tachyarrhythmia and operating the switch network to select an electrode configuration suitable for the identified tachyarrhythmia, which logic circuits also function in accordance with the present invention to operate the switch network to disconnect the atrial electrode, and more preferably to replace the atrial electrode connection with an external electrode. In an alternate embodiment, the switch network can implement the control function to select the electrode configuration in response to an identified tachyarrhythmia, such that the switch network operates to disconnect the atrial electrode in accordance with the present invention.

BRIEF DESCRIPTION OF THE DRAWINGS

Other characteristics and advantages of the present invention will appear to the person of ordinary skill in the art, in view of the following description, made with reference to the annexed drawings, in which FIG. 3 is a table of switch states for the circuit of FIG. 2.

DETAILED DESCRIPTION OF THE DRAWING

Figure 1:
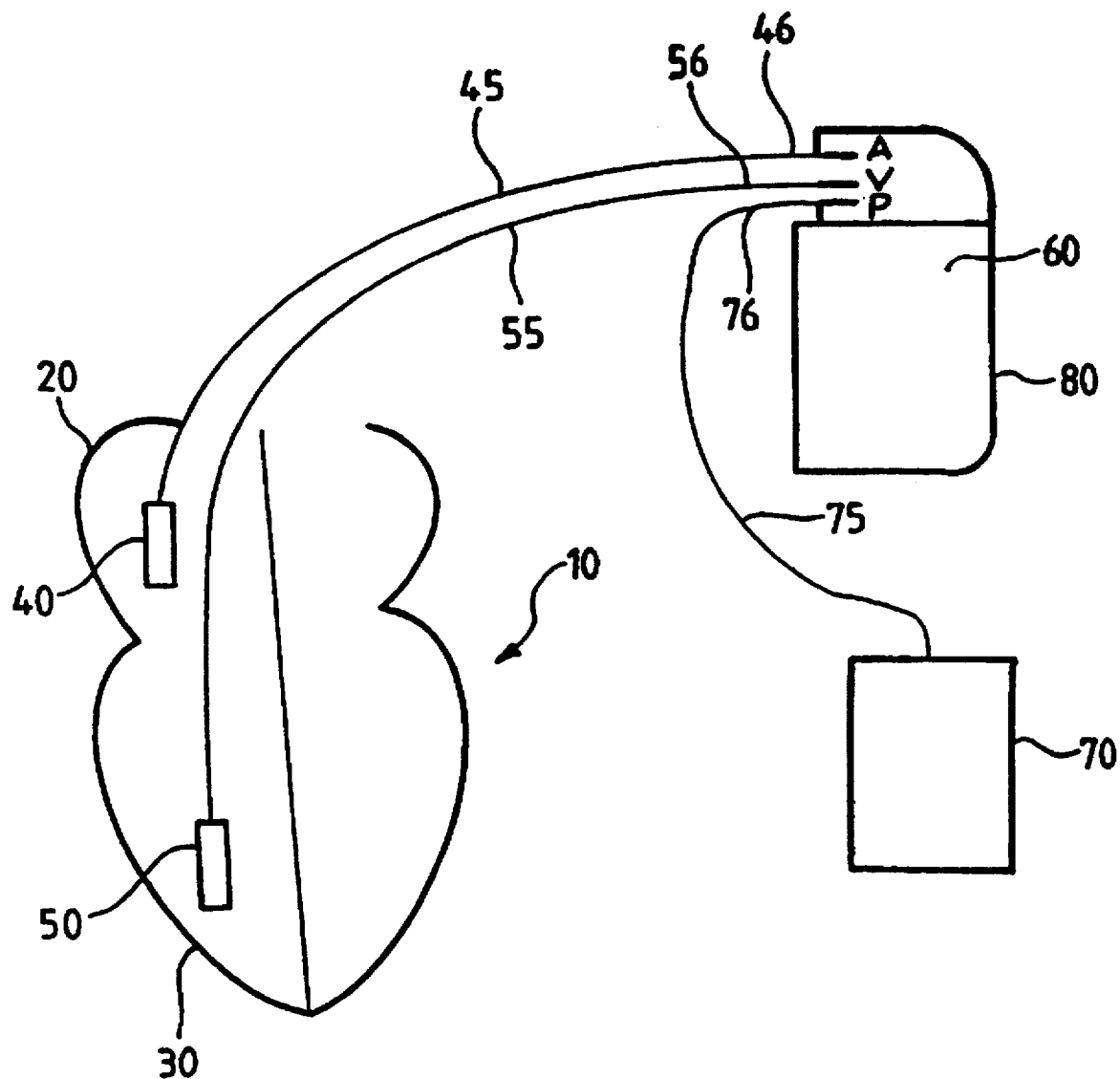
FIG. 1 represents in a schematic manner a device according to the invention (that is, a pulse generator and lead system of electrodes) implanted in the heart of a patient.

With reference to FIG. 1, the reference 10 designates the heart, with its atrial cavity 20 and its ventricular cavity 30. The implanted device comprises a pulse generator 60 and a lead system of electrodes, which comprises an atrial electrode 40 and a ventricular electrode 50. The atrial electrode 40 is placed in the vicinity of or inside the atrium 20 and is connected to the generator 60 by a lead (probe) 45, which is connected to an input/output terminal 46 of the pulse generator 60. The ventricular electrode 50 is placed in the right ventricle 30 and connected to the generator 60 by a lead (probe) 55, which is connected to an input/output terminal 56 of the pulse generator 60.

In an optional embodiment, an external electrode also is used. The external electrode may be a "patch" electrode 70 which is connected by a lead (probe) 75 to an output 76 of the pulse generator, or a metallic case 80 of the pulse generator 60. More preferably, at least one of the external electrodes 70 and 80 can be used to insure the return of the shock current during the application of the shock energy pulse, and further, the two external electrodes 70 and 80 can, if desired, be used simultaneously.

All these elements and their uses and roles in treating cardiac tachyarrhythmia are well known in the prior art and, therefore, do not necessitate a more detailed description. Indeed, almost any form and type of such electrodes, switch network, and control logic can be used in implementing the present invention.

The implanted device of the present invention thus can send to the heart high energy pulses (cardioversion or defibrillation) according to various electrode configurations by appropriate commutations of the lead system that are realized by the analog and/or digital logic circuits of the pulse generator 60.

FR-A-2,711,064 describes a suitable manner in which these different commutations can be, on the one hand, chosen to optimize the effect of the shock and, on the other hand, realized electrically, for example, use of a switch network comprised of solid state switch components such as MOSFETs (metal on silicon field effect transistors), IGBTs (insulated gate bipolar transistors), SCRs (silicon controlled rectifiers), or combinations thereof, or analogous components. FR-A-2,711,064 has a corresponding U.S. Pat. No. 5,545,181, which is commonly assigned, the disclosure of which is incorporated herein by reference in its entirety.

With reference to FIG. 1, the various possible electrode configurations discussed above are the following:

a) a shock pulse that is delivered between electrodes 40 and 50, b) a shock pulse that is delivered between the electrode 50 and either the electrode 70 or the electrode 80; and, in another embodiment of this configuration, a shock pulse that is delivered between, on the one hand, the electrode 50, and, on the other hand, electrodes 70 and 80 electrically connected together, which commutation is performed by the action of the internal logic of the generator 60 on the solid state switch components;

c) a shock pulse that is delivered between, on the one hand, the electrode 50, and, on the other hand, electrodes 40 and 80 electrically connected together, although in another embodiment of this configuration, the electrode 70 can be connected to the subsystem formed by electrodes 40 and 80;

d) a shock pulse that is delivered between, on the one hand, electrodes 40 and 50 electrically connected together and, on the other hand, the electrode 70 or the electrode 80, and in another embodiment of this configuration, electrodes 70 and 80 can be electrically connected together. All connections of electrodes are decided and executed under the action of the internal logic of the pulse generator 60, which, as is well known, may be a software-controlled microprocessor device or a solid state machine having dedicated logic circuits.

The invention thus applies in the case of FIG. 1 in which a cardioversion shock has to be applied. In this case, in a first step, the internal logic of the generator 60 disconnects the input/output terminal 46, so that the atrial electrode 40 has a potential that is floating with respect to the rest of the device, namely floating potential with respect to the reference or ground potential, which may be a negative or a positive voltage. In a second step, the internal logic examines what would have been the electrodes configuration normally chosen, that is to say, the configuration which is most appropriate for the situation of the patient according to the usual selection criteria.

If, in the configuration that would have been normally chosen, the electrode 40 should have served as a return electrode for the shock current, then one modifies the electrode configuration to substitute for the atrial electrode 40 an external electrode, namely the electrode 80 and/or the electrode 70, as the return electrode. If, on the other hand, the configuration normally chosen does not imply the utilization of the electrode 40 as the return electrode, then one does not modify the selected configuration which remains as initially programmed.

Of course, it should be well understood that when one has to deliver a defibrillation shock, that is to say a shock of an even higher energy than a cardioversion shock, the atrial electrode 40 is automatically connected again to the device so as to offer all of the defibrillation shock delivery electrode configurations a), b), c) and d), the particular technique of the invention concentrating only in the case of the deliverance of a cardioversion shock.

The disconnection of the input/output terminal 46 can be operated by a device of the same type as that disclosed in the aforementioned FR-A-2 711 064 (U.S. Pat. No. 5,545,181), the only modification being in the control logic, whose programming has to be adapted in a manner to realize the actions described above. Such a modification in programming is believed to be easily accomplished by a person of ordinary skill in the art and, therefore, need not be described in more detail.

Figure 2:
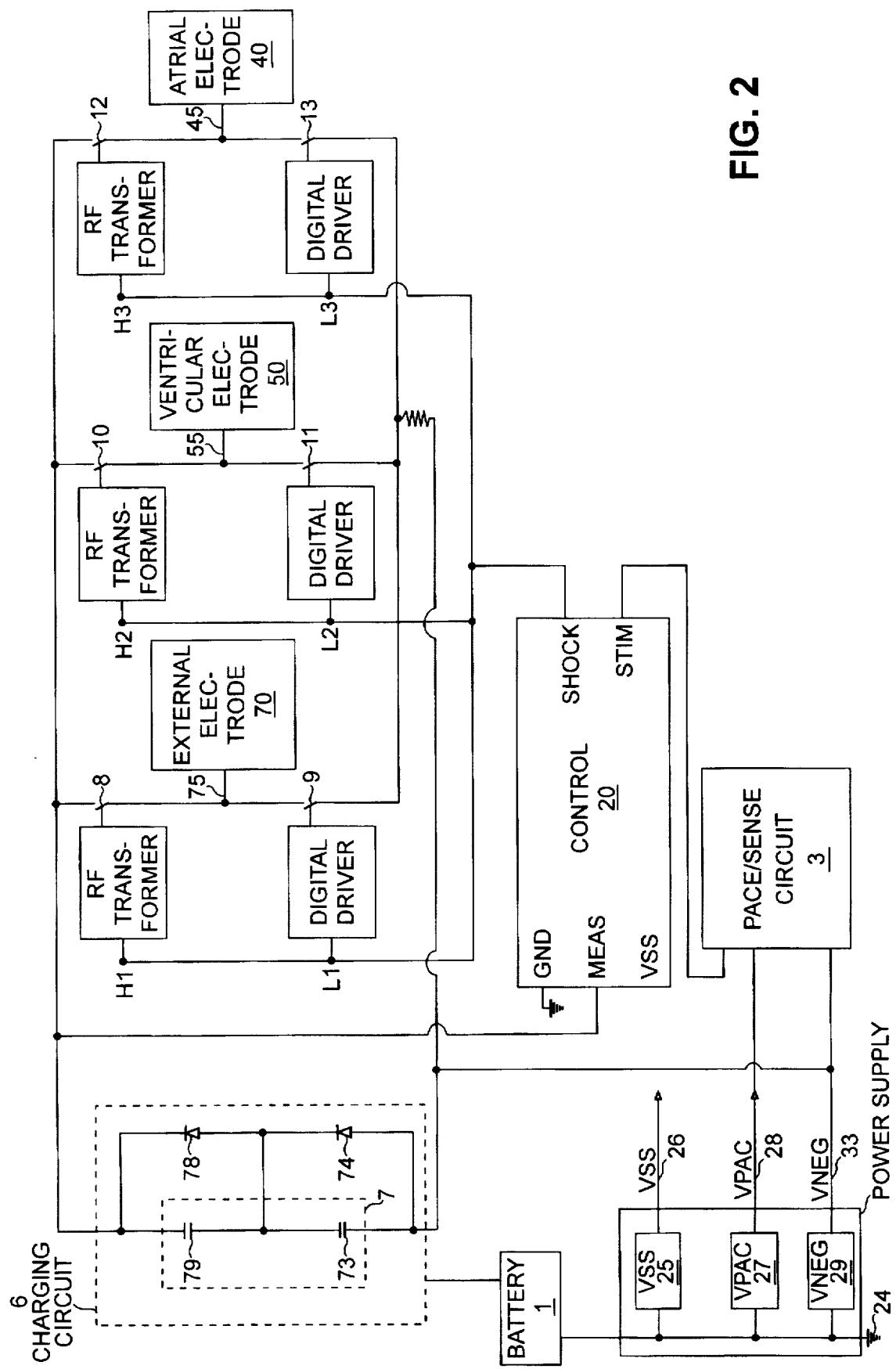
FIG. 2 is a schematic drawing of a circuit in accordance with a preferred embodiment of the invention.

Referring to FIG. 2, a circuit of a switch network 100 for selectively connecting each of the atrial (A) electrode 40, ventricular (V) electrode 50 and external (P) electrode 70 to the pulse generator output. Circuit 100 uses, for each electrode, a high side switch H and a low side switch L. Thus, the external electrode 70 is connectable to either end of a shock capacitor 7 (including two series capacitors 79 and 73, each having a diode 78 and 74 in parallel therewith) by closing one of high side switch H1, or low side switch L1, depending on the direction the shock is to flow. Similarly, ventricular electrode 70 is connectable to either end of shock capacitor 7 by high side switch H2 and low side switch L2, and atrial electrode is connectable to either end of shock capacitor 7 by high side switch H3 and low side switch L3

Referring to FIG. 3, a Table of switch states is shown which indicates the polarity of current flow between a desired pair or combination of electrodes, in which two electrodes may be connected in parallel. The switch state "0" in FIG. 3 indicates an open switch, and a "1" indicates a closed switch.

The FIG. 2 also shows a power supply circuit 23 for supplying power from battery 1 to control circuits 2, and low side drivers L1, L2 and L3. Power supply 23 includes:

A connection 24 from the positive terminal of battery 1 to ground,

A VSS supply circuit 25 for deriving a first negative supply voltage called VSS at 26 for powering control circuits 2 between VSS and ground, for serving as a logic reference level throughout the device, and for powering high side drivers H1, H2, and H3, A VPAC supply circuit 27 for deriving a second negative supply voltage called VPAC at 28 for powering pace/sense circuits 3 between VPAC and ground, A VNEG supply circuit 29 for deriving a third negative supply voltage called VNEG at 33, for powering low side drivers L1, L2, and L3 between VNEG and ground, and A connection 31 from VNEG, to the negative terminal of single capacitor 7A, 7B and to the shock circuit 32 via optional sensing resistor 41. The value of resistor 41 is very low, approximately 0.03 Ohms, and there is essentially zero voltage across it during normal operation of the circuit.

Preferably, in the power supply 23: VSS at 26 is approximately 1.0 to −3.0 V, VAPC at 28 is approximately −0.5 to −10 V, the value of which is optionally programmable, and VNEG at 33 is approximately −10 to −15 V.

Numerous alternate configurations of power supply 23 and its component circuits or providing the first (VSS), second (VPAC) and third (NEG) negative supply voltages, and their constructions, exist within the scope of the invention and the abilities of a person of ordinary skill in the art. FIG. 2 shows one such configuration having three separate regulated supplies 25, 27 and 29, each operating directly from the battery. Examples of alternative configurations include: (1) connecting one or more of the supply outputs directly to the battery negative terminal without regulation, (2) connecting one or more of the supply outputs to a single regulator, or (3) deriving second and third voltages from the battery and/or the first regulated voltage, using, for example, voltage multipliers or level shifters.

Referring still to FIG. 2, pace/sense circuits 3 include logic operating between ground and VSS, and pacing signal generation (i.e., the stimulation pulse) operating between ground and VPAC. The circuits 3 may also use VNEG which is always at least as negative as VPAC, to provide a common mode operating region including VPAC.

The charging circuit 6 charges capacitor 7 (i.e., capacitors 7A and 7B ) to a preset voltage determined by regulating means not shown here, but which are well known, and shown in numerous examples, in the prior art. One useful charging circuit is disclosed in copending and commonly assigned U.S. patent application Ser. No. 08/287,834, filed Aug. 9, 1994 in the name of Peter Jacobson, the disclosure of which is incorporated herein by reference.

Switches 8 to 13 can be implemented as MOSFETs, IGBTs, or SCRs, as familiar to designers skilled in the art. Since SCRs cannot be turned off until current through them falls to zero, they can only be used in either the high or low side switch for one phase, but not in both sides in the same phase. MOSFETs or IGBTs should have series diodes as shown in the prior art, to prevent external defibrillation from being conducted in the opposite direction through the switches.

Low side switch drivers L1, L2, and L3 translate a logic level signal between VSS and GND to a more negative signal between VNEG and GND. High side switch drivers H1, H2, H3 translate a logic level signal between VSS and GND to provide an isolated control signal output. Examples using pulse transformers for SCR switches, or RF transformers for MOSFET or IGBT switches, are well known and shown in the prior art.

One skilled in the art will appreciate that the present invention can be practiced by other than the described embodiments, which are presented for purposes of illustration and not of limitation.

I claim:

1. An active implantable medical device comprising:

an atrial electrode to be placed in the vicinity of or inside the atrium;

a ventricular electrode to be placed inside the ventricle;

at least one external electrode adapted to be placed external to the heart; and a pulse generator case, comprising:

means for delivering a shock pulse energy, and means for switchably connecting said atrial, ventricular and at least one external electrodes to the delivering means in an electrode configuration to deliver a shock energy pulse, wherein the switchably connecting means further comprises means, responsive to a delivery of a shock energy, for disconnecting said atrial electrode from the delivering means and, in response to said configuration having said atrial electrode switched to the delivering means, connecting said at least one electrode external to the delivering means in place of the disconnected atrial electrode.

2. An active implantable medical device comprising:

a pulse generator having shock energy pulse output, the shock energy pulse output having one of a cardioversion shock energy level and a defibrillation shock energy level;

a control logic circuit operable to select one of the cardioversion shock energy level and the defibrillation shock energy level and to select an electrode configuration appropriate for said selected shock energy level;

an atrial electrode to be placed in the vicinity of the atrium;

a ventricular electrode to be placed in the ventricle;

at least one external electrode to be placed external to the heart;

a switch network coupled to said shock energy pulse generator, said atrial electrode, said ventricular electrode, and said at least one external electrode, the switch network having a plurality of electrode configurations for connecting selected ones of said atrial, ventricular and external electrodes to said pulse generator to deliver said selected shock energy pulse to the heart, at least one of said plurality of configurations having the atrial electrode connected to the pulse generator, wherein in response to a selected cardioversion shock energy level and a selected electrode configuration in which the atrial electrode is connected to the pulse generator as a return electrode, the switch network is operated to disconnect the atrial electrode from said pulse generator.

3. The device of claim 2 wherein the switch network further comprises a plurality of solid state switch elements selected from among the group consisting of MOSFETs, IGBTs, and SCRs, the plurality of solid state switches selectively connecting the atrial, ventricular and external electrodes to said pulse generator.

4. The device of claim 2 wherein the control logic operates said switch network in response to a selected defibrillation shock energy pulse and a selected electrode configuration in which the atrial electrode is connected to the pulse generator not to disconnect the atrial electrode from said pulse generator.

5. The device of claim 2 wherein the control logic operates said switch network to connect at least one of said external electrode to said pulse generator in place of said disconnected atrial electrode.

6. A method for delivering shock energy pulse to a patient comprising:

a) providing an active medical device having an atrial electrode in the vicinity of the atrium, a ventricular electrode in the electrode and at least one electrode external to the heart, comprising:

b) selecting a shock energy pulse is appropriate to revert an arrhythmia condition;

c) selecting a configuration of said atrial, ventricular and at least one external electrode appropriate for delivering the selected shock energy pulse wherein step c) further comprises:

i determining if the selected shock energy pulse corresponds to a cardioversion shock pulse energy, and, in response thereto, determining if the selected electrode configuration has the atrial electrode connected to the shock pulse generator; and ii in response to the atrial electrode being connected to the shock pulse generator and the selected shock pulse being a cardioversion pulse, disconnecting the atrial electrode from said pulse generator during delivery of said cardioversion shock pulse.

7. The method of claim 6 wherein step c)ii further comprises connecting at least one external electrode to said pulse generator in place of said atrial electrode during delivery of said cardioversion shock pulse.

8. The method of claim 6 wherein the pulse generator has a ground potential and step c)ii further comprises allowing the atrial electrode to have a potential that floats relative to said ground potential.

* * * * *

UNITED STATES PATENT AND TRADEMARK OFFICE
CERTIFICATE OF CORRECTION

PATENT NO. : 5,776,165
DATED : July 7, 1998
INVENTOR(S) : Ripart

It is certified that error appears in the above-identified patent and that said Letters Patent is hereby corrected as shown below:

Column 1, line 11, after "say" insert --will--;
Column 1, line 26, after "susceptible" delete "be" and insert --being--;
Column 3, line 5, after "generator" insert --,--;
Column 3, line 13, after "addition" insert --,--;
Column 4, line 30, after "and" delete "50", and insert --50;--;
Column 4, line 44, after "and 80;" insert --and--;
Column 4, line 50, before "All connections of electrodes" insert --[ new ¶, i.e., ¶ break]--;
Column 5, line 5, after "namely" insert --,--;
Column 5, line 12, after "say" insert --,--;

Column 7, line 3, change "electrodes" to --electrode--;

Abstract, line 2 change "defibrillatory" to --defibrillator/--;
Title, after "DEFIBRILLATOR" insert --/--;

Signed and Sealed this

Third Day of October, 2000

*Attest:*

Q. TODD DICKINSON

*Attesting Officer*    *Director of Patents and Trademarks*